US006660883B1

(12) United States Patent
Chaudhari et al.

(10) Patent No.: US 6,660,883 B1
(45) Date of Patent: Dec. 9, 2003

(54) PROCESS FOR THE PREPARATION OF 2-ARYL PROPIONIC ACIDS

(75) Inventors: Raghunath Vitthal Chaudhari, Pune (IN); Jayasree Seayad, Pune (IN); Abdul Seayad, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/662,035

(22) Filed: Sep. 14, 2000

(51) Int. Cl.[7] .......................... C07C 51/14; C07C 51/16
(52) U.S. Cl. ...................... 562/406; 562/408; 562/409
(58) Field of Search ................................ 562/406, 408, 562/409

(56) References Cited

U.S. PATENT DOCUMENTS

| 3,700,729 | A | * | 10/1972 | Fenton |
| 4,034,004 | A | * | 7/1977 | Cassar et al. |
| 4,212,989 | A | * | 7/1980 | Isshiki et al. |
| 4,255,591 | A | * | 3/1981 | Makin et al. |
| 4,433,166 | A | * | 2/1984 | Singleton et al. |
| 4,582,929 | A | * | 4/1986 | DeVries |
| 4,681,707 | A | * | 7/1987 | Alper et al. |
| 4,733,006 | A | * | 3/1988 | Singleton et al. |
| 4,843,172 | A | * | 6/1989 | Tanaka et al. |
| 4,937,362 | A | * | 6/1990 | Tanaka et al. |
| 4,981,995 | A | * | 1/1991 | Elango et al. ............... 562/406 |
| 5,158,921 | A | * | 10/1992 | Drent et al. |
| 5,237,097 | A | * | 8/1993 | Smith et al. |
| 6,093,847 | A | * | 7/2000 | Chaudhari et al. |

FOREIGN PATENT DOCUMENTS

EP     0338852      * 4/1989

* cited by examiner

Primary Examiner—Alan L. Rotman
Assistant Examiner—Taylor V Oh
(74) Attorney, Agent, or Firm—Ladas and Parry

(57) ABSTRACT

The present invention provides an improved process for the preparation of 2-aryl propionic acid which by subjecting an aryl compound selected from an aryl alcohol or aryl halide or an aryl olefin to carbonylation in the presence of a halide source, a protonic acid, water and a heterogeneous metal and a phosphine ligand as a catalyst in an organic solvent.

21 Claims, No Drawings

PROCESS FOR THE PREPARATION OF 2-ARYL PROPIONIC ACIDS

This invention relates to an improved process for the preparation of 2-aryl propionic acids. Particularly this invention relates to an improved, process for conversion of aryl alkyl compound such as aryl alkyl alcohols and aryl alkyl halides having the general formula I

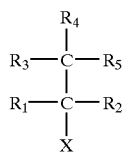

I or aryl olefins of the general formula II

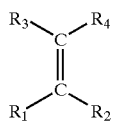

II wherein, $R_1$ may be aryl, substituted aryl, naphthyl or substituted naphthyl, $R_2$, $R_3$, $R_4$ and $R_5$ may independently be hydrogen, alkyl, aryl, arylalkyl, cycloaliphatic with or without substituents, and X is a halogen atom or an —OH group, to the corresponding 2-aryl propionic acids using a catalyst system based on a heterogeneous metal selected from palladium, platinum, rhodium, iridium, ruthenium, cobalt or nickel.

A majority of the 2-aryl propionic acids are well known non-steroidal anti-inflammatory drugs. The conventional synthesis of ibuprofen involves six steps, which use hazardous chemicals like sodium cyanide and the waste materials produced require down stream treatments for disposal. Recently, Hoechst Celanese Corporation has developed a novel environmentally benign three step catalytic route for the synthesis of ibuprofen, in which carbonylation of para isobutyl phenyl ethanol is the key step. In the processes described in patented literature, the catalysts used were mainly Pd(PPh$_3$)Cl$_2$ or PdCl$_2$ or Pd(OAc)$_2$ alongwith excess phosphate legends (EP 0,400,892 A3, EP 0,284,310 A1), which gave lower reactions rates (TOF=25–35 h$^{-1}$) and lower selectivity to ibuprofen (56–69%) under mild conditions (130° C., 1000 psig.). Higher selectivity (>95%) was obtained only at very high pressure of 2000 to 4500 psig and the rates still remained low, U.S. Pat. No. 5,536,874 and the publication J. Chem. Tech. Biotechnol, 1997, 70, 83–91 describe the carbonylation of p-IBPE in a two phase system wherein one phase is an aqueous medium which contains a water soluble palladium complex and an acid promoter. These processes also have disadvantages such as low reaction rates (TOF-0.1 to 0.4 h$^{-1}$) and lower ibuprofen selectivity (59–74%) under mild reaction conditions (90° C., 450 to 900 psig). EP 387502 (1990) and EP 361021 (1990) report the use of homogeneous Nickel catalysts but only in the presence of corrosive iodide promoters and gives low reaction rates and selectivity under even high pressure conditions. GB patent 2199030A (1988), JP 02 164 841 (1990) and JP 63 162 654 (1988) disclose homogeneous Rh complex catalysts for the carbonylation of α-phenyl ethyl alcohol derivatives. However, these give very low reaction rates and use iodide promoters.

Another pathway to 2-aryl propionic acids which is more rewarding is the carbonylation of aryl olefins which can be easily obtained from the catalytic cracking of corresponding saturated hydrocarbons and is more economical. Ali and Alper have reported in a publication J. Mol. Catal. 1992, 77, 7–13, the carbonylation of aryl olefins using Pd(OAc)$_2$/dppb/PPh$_3$/HCOOH catalyst system. But the reaction rate (TOF=2.2 h$^{-1}$) and 2-aryl propionic acid selectivity (15–20%) were too low, the major product being the 3-aryl propionic acid. More recently, U.S. Pat. No. 5,260,477 disclosed a process for the carbonylation of p-isobutyl styrene to ibuprofen using PdCl$_2$(PPh$_3$)$_2$/10% HCl, under very high CO pressures (300 bar at 120° CO which again have a low reaction rate (TOF=~25 h$^{-1}$) and ibuprofen selectivity (89%). Another U.S. Pat. No. 5,315,026 reported the carbonylation of p-isobutyl styrene to ibuprofen using a PdCl$_2$/CuCl$_2$/(+)-neomethyl diphenylphosphine/10% HCl catalyst system which gave good ibuprofen selectivity (<98%), but a very low reaction rate (TOF=~25 h$^{-1}$) under 30–200 psig CO pressure at 100° C. the publications New J. Chem. 1997, 21, 529–531 and Catal. Lett., 1997, 47, 43–46 revealed the carbonylation of aryl olefins to 2-aryl propionic acid using a biphasic catalyst system (PdCl$_2$/TPPTS) under 50 bar CO pressure at 65–100° C. which also gave low reaction rates (25–50 h$^{-1}$) and low selectivity (60–75%). Other major problem of these processes is the difficulty of catalyst separation and recycle.

The inventors of the present invention have observed that the use of a new catalyst system based on a heterogeneous metal selected from palladium, platinum, rhodium, iridium, ruthenium, cobalt or nickel, a phosphine ligand, a protonic and a halide source provide an improved catalyst system for the carbonylation of compounds of general formula I or II to corresponding 2-arylpropionic acids. The use of such a catalyst system gives high reaction rates and high selectivity to 2-arylpropionic acids under mild reaction conditions with easy separation of an efficient recycle of the catalyst. Another added advantage is metals such as ruthenium, cobalt or nickel are low cost metals.

The object of the present invention therefore is to provide an improved process for the preparation of 2-aryl propionic acids by the carbonylation of corresponding alcohols, aryl alkyl halides or olefins.

Accordingly, the present invention provides an improved process for the preparation of 2-aryl propionic acid which comprises subjecting to carbonylation, an aryl compound selected from an aryl alcohol or aryl halide having the general formula I or an aryl olefin having the general formula II, wherein $R_1$, may be aryl, substituted aryl, naphthyl or substituted naphthyl, $R_2$, $R_3$, $R_4$ and $R_5$ independently be hydrogen, alkyl, aryl, arylalkyl, cycloaliphatic with or without substituents in the presence of a halide source, a protonic acid, water and a heterogeneous metal selected from palladium, platinum, rhodium, iridium, ruthenium, cobalt or nickel, and a phosphine ligand as a catalyst in an organic solvent such as herein described in carbon monoxide atmosphere, at a temperature between 30 to 130° C., for a period ranging between 0.3. to 24 hrs, at pressures ranging between 50 to 1500 psig, cooling the reaction mixture to ambient temperature, flushing the reaction vessel with inert gas, separating the catalyst, removing the solvent by conventional methods, and isolating 2-aryl propionic acid of formula III wherein, $R_1$ may be aryl, substituted aryl, naphthyl or substituted naphthyl, $R_2$, $R_3$, $R_4$ and $R_5$ may independently be hydrogen, alkyl, aryl, arylalkyl, cycloaliphatic with or without substituents.

It is preferred, that $R_1$ is phenyl, naphthyl, or substituted phenyl or substituted naphthyl, for example, 4-isobutylphenyl, 4-methylphenyl, 4-chlorophenyl, 4-bromophenyl, 4-cyanomethyl, 4-tert-butylphenyl, 4-hydroxyphenyl, or 6-methoxy naphthyl.

It is preferred that $R_2$, $R_3$, $R_4$ and $R_5$ are independently hydrogen, methyl or substituted methyl.

In one of the embodiments of the present invention, the catalyst used may be palladium, platinum, rhodium, iridium, ruthenium, cobalt or nickel as metal powder or as supported metal form.

In another embodiment the supports used may be carbon, or any of the refractory oxides such as γ-alumina, silica, titania, zirconia, or clays, and zeolites.

In yet another embodiment the phosphine ligand used may be any of the mono or diphosphines such as triphenyl phosphine, tris(p-tolyl)phosphine, tricyclohexyl phosphine, tris(p-chloro phenyl)phosphine, tris(p-fluoro phenyl) phosphine, tris(p-methoxy phenyl)phosphine, tributyl phosphine, trisisopropyl phosphine, bisdiphenyl phosphino ethane, bisdiphenyl phosphino propane and bisdiphenyl phosphino butane.

In another embodiment the halide source may be any of the halide salts such as lithium chloride, sodium chloride, potassium chloride, lithium iodide, lithium bromide, sodium bromide, sodium iodide, potassium bromide, potassium iodide, tetrabutyl ammonium chloride, tetrabutyl ammonium bromide and tetrabutyl ammonium iodide or hydro halic acids such as hydrochloric acid, hydrobromic acid and hydro iodic acid.

In yet another embodiment the protonic acid used may be any of the hydrohalic acids such as hydrochloric acid, hydrobromic acid and hydroiodic acid or other portonic acids such as para toluene sulphonic acid, methane sulphonic acid, trifluoromethane sulphonic acid, formic acid, oxalic acid, acetic acid and trifluoro acetic acid.

In yet another embodiment the organic solvent may be the, aromatic hydrocarbons like benzene, toluene, xylenes, or ketones like methyl ethyl ketone, acetone or cyclic ethers such as tetrahydrofuran, dioxan, or nitriles such as acetonitrile or amides like N-methyl pyrrolidone.

In another embodiment the concentration of catalyst may be one mole of the metal for every 500 to 50000 moles of said aryl compound of formula I or II, preferably 1 mole for every 800 to 20000 moles, and more preferably one mole for every 1000 to 15000 moles.

In still another embodiment the amount of halide source per gram mole or metal may be in the range of 50 to 10000 moles, preferably 100 to 8000 moles, and more preferably 500 to 6000 moles.

In another embodiment the amount of acid source per gram mole of metal may be in the range of 50 to 10000 moles, preferably 100 to 8000 moles, and more preferably 500 to 6000 moles.

In yet another embodiment the amount of the phosphine ligand per gram mole of metal may be in the range of 20 to 250.

In yet another embodiment the amount of water may be in the range of 1 to 6% (v/v) of the total reaction mixture, preferably 3 to 5% (v/v).

In a feature of the invention, the reaction can be conveniently carried out in a stirred reactor with the improved catalyst employed with a suitable solvent in presence of carbon monoxide.

The improved process of the present invention is described herein below with examples, which are illustrative only and should not be construed to limit the scope of the present invention in any manner.

EXAMPLE 1

Preparation of 1% Pd/C: 0.0167 g of $PdCl_2$ was dissolved in 10 ml of 1N HCl. After complete dissolution of $PdCl_2$ the solution was diluted to 30 ml and 1 g of activated charcoal was added to make slurry, which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C., the catalyst was filtered, washed thoroughly with warm water several times, and dried under vacuum at 60° C.

EXAMPLE 2

Preparation of 1% Pd/γ-Alumina: 0.0167 g of $PdCl_2$ was dissolved in 10 ml of 1N HCl. After complete dissolution of $PdCl_2$ the solution was diluted to 30 ml and 1 g of activated γ-Alumina was added to make a slurry which was kept under vigorous stirring at room temperature. After 6 hours the slurry was heated to 80° C. in a water bath. After attaining the temperature the pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 3

Preparation of Pd/ZSM 5: 0.0167 g of $PdCl_2$ was dissolved in 10 ml of 1N HCl. After complete dissolution of $PdCl_2$ the solution was diluted to 30 ml and 1 g of H-ZSM 5 was added to make a slurry which was kept under vigorous stirring at room temperature. After 6 hours the slurry was heated to 80° C. in a water bath. After attaining the temperature of pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 4

Preparation of Pd metal: 0.1 g of $PdCl_2$ was dissolved in 10 ml of 1 N HCl. After complete dissolution of $PdCl_2$ the solution was diluted to 30 ml and 10 ml of hydrazine hydrate solution was added drop wise under stirring, precipitating the Pd metal out, which was filtered, washed several times with warm water and dried under vacuum. Yield –98%.

EXAMPLE 5

Preparation of 1% Pt/C: 0.0136 g of $PtCl_2$ was dissolved in 5 ml of 5N HCl. After complete dissolution of $PtCl_2$ the solution was diluted to 30 ml and 1 g of activated charcoal was added to make a slurry which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C. the catalyst was filtered, washed thoroughly with warm water several times, and dried under vacuum at 60° C.

EXAMPLE 6

Preparation of 1% Rh/C: 0.025 g of $RhCl_3.3H_2O$ was dissolved in 30 ml of distilled water. 1 g of activated charcoal was added to this solution make a slurry, which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C., the catalyst was filtered, washed thoroughly with warm water several times, and dried under vacuum at 60° C.

EXAMPLE 7

Preparation of 1% Rh/γ-Alumina: 0.025 g of RhCl$_3$.3H$_2$O was dissolved in 30 ml of distilled water. 1 g of γ-Alumina was added to this solution make a slurry, which was kept under vigorous stirring at room temperature. After 6 hours the slurry was heated to 80° C. in a water bath. After attaining the temperature the pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 8

Preparation of 1% Rh/ZSM 5: 0.025 g of RhCl$_3$.3H$_2$O was dissolved in 30 ml of distilled water. 1 g of H-ZSM 5 was added to this solution to make a slurry which was kept under vigorous stirring at room temperature. After 6 hours the slurry was heated to 80° C. in a water bath. After attaining the temperature of pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 9

Preparation of 1% Ir/C: 0.0184 g of IrCl$_3$ was dissolved in 30 ml of distilled water. 1 g of activated charcoal was added to this solution to make a slurry which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C. the catalyst was filtered, washed thoroughly with warm water several times, and dried under vacuum at 60° C.

EXAMPLE 10

Preparation of 1% Ru/C: 0.0167 g of RuCl$_3$ was dissolved in 30 ml of distilled water. 1 g of activated charcoal was added to this solution make a slurry, which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C., the catalyst was filtered, washed thoroughly with warm water several times, and dried under vacuum at 60° C.

EXAMPLE 11

Preparation of 1% Ni/C: 0.0167 g of NiCl$_2$ 6H$_2$O was dissolved in 30 ml of distilled water. 1 g of activated charcoal was added to this solution make a slurry, which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C., the catalyst was filtered, washed thoroughly with warm water several times, and dried under vacuum at 60° C.

EXAMPLE 12

Preparation of 1% Co/C: 0.0167 g of CoCl$_2$ 6H$_2$O was dissolved in 30 ml of distilled water. 1 g of activated charcoal was added to this solution make a slurry, which was kept under vigorous stirring at room temperature. After 6 hours the slurry was heated to 80° C. in a water bath and 8 ml of 40% formaldehyde solution was added followed by addition of 2N NaOH solution to make the medium basic (pH=10–12). After 1 hour stirring at 80° C., the catalyst was filtered, washed thoroughly with warm water several times, and dried under vacuum at 60° C.

EXAMPLE 13

Preparation of 1% Ru/γ-Alumina: 0.0167 g of RuCl$_3$.3H$_2$O was dissolved in 30 ml of distilled water. 1 g of γ-Alumina was added to this solution make a slurry, which was kept under vigorous stirring at room temperature. After 6 hours the slurry was heated to 80° C. in a water bath. After attaining the temperature the pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 14

Preparation of 1% Ni/γ-Alumina: 0.0167 g of NiCl$_2$.6H$_2$O was dissolved in 30ml of distilled water. 1 g of γ-Alumina was added to this solution make a slurry, which was kept under vigorous stirring at room temperature. After 6 hours the slurry was heated to 80° C. in a water bath. After attaining the temperature the pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 15

Preparation of 1% Co/γ-Alumina: 0.0167 g of CoCl$_2$.6H$_2$O was dissolved in 30 ml of distilled water. 1 g of γ-Alumina was added to this solution make a slurry, which was kept under vigorous stirring at room temperature. After 6 hours the slurry was heated to 80° C. in a water bath. After attaining the temperature the pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 16

Preparation of 1% Ru/H-ZSM 5: 0.0167 g of RuCl$_3$.3H$_2$O was dissolved in 30 ml of distilled water. 1 g of H-ZSM 5 was added to this solution to make a slurry which was kept under vigorous stirring at room temperature. After 6 hours the slurry was heated to 80° C. in a water bath. After attaining the temperature of pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 17

Preparation of 1% Ni/H-ZSM 5: 0.0167 g of NiCl$_2$.6H$_2$O was dissolved in 30 ml of distilled water. 1 g of H-ZSM 5 was added to this solution to make a slurry which was kept under vigorous stirring at room temperature. After 6 hours the slurry was heated to 80° C. in a water bath. After attaining the temperature of pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 18

Preparation of 1% Co/H-ZSM 5: 0.0167 g of $CoCl_2.6H_2O$ was dissolved in 30 ml of distilled water. 1 g of H-ZSM 5 was added to this solution to make a slurry which was kept under vigorous stirring at room temperature. After 6 hours the slurry was heated to 80° C. in a water bath. After attaining the temperature of pH of the solution was made 4.5 by adding enough quantities of 1 N NaOH solution. There after 10 ml of 1 N solution of sodium formate was added. After 1 hour stirring at 80° C., the catalyst was filtered, washed thoroughly with warm water several times, and dried at 120° C.

EXAMPLE 19

A 50 ml stirred autoclave was charged with the following reactants 1-(4-isobutylphenyl) ethanol: 2.5 g
1%Pd/C: 0.1 g
triphenyl phosphine: 0.08165 g
p-toluene sulphonic acid: 1.06 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 770 $h^{-1}$ and 99% conversion of p-IBPE with ibuprofen selectivity of 98.2%. The catalyst was filtered out and the solvent evaporated and the reaction mixture re-dissolved in toluene. The precipitated solid which a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation and vacuum distillation gives the pure product.

EXAMPLE 20

A 50 ml stirred autoclave was charged with the following reactants 1-(4-isobutylplhenyl)ethanol: 2.5 g
1% Pd/C (separated from example 19): 0.056 g
triphenyl phosphine: 0.08165
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The rector was then cooled and the liquid phase analysed by gas chromatography.

The GC analysis showed TOF of 800 $h^{-1}$ and 98% of p-IBPE with ibuprofen selectivity of 98%. The catalyst was filtered out, the solvent evaporated and the reaction mixture re-dissolved in toluene. The solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation and vacuum distillation gives the pure product.

EXAMPLE 21

A 50 ml stirred autoclave was charged with the following reactants 1-(4'-isobutylphenyl)ethanol: 2.5 g
1% Pd/C (separated from example 19) 0.042 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 790 $h^{-1}$ and 99% conversion of p-IBPE with ibuprofen selectivity of 98%. The catalyst was filtered out, the solvent evaporated and the reaction mixture re-dissolved in toluene. The solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation and vacuum distillation gives the pure product.

EXAMPLE 22

A 50 ml stirred autoclave was charged with the following reactants 1-(4'-isobutylphenyl)ethanol: 2.5 g
1% Pt/C: 0.1 g
triphenyl phosphine: 0.08165 g
p-toluene sulphonic acid: 1.065

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commended immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 370 h$^{-1}$ and 99% conversion of p-IBPE with ibuprofen selectivity of 99.2%. The catalyst was filtered out and the solvent evaporated and the reaction mixture re-dissolved in toluene. The precipitated solid portion, which is a mixture of LiCl and lithium slat of p-toluene sulphonic acid was filtered out. The filtrate is treated with saturated solution of sodium bicarbonate two–three times and the aqueous phase is separated to obtain the sodium slat of ibuprofen, which on hydrolysis with acid and extraction with dichloromethane, evaporation and vacuum distillation gives the pure product.

EXAMPLE 23

A 50 ml stirred autoclave was charges with the following reactants 1-(4'-isobutylphenyl)ethanol: 2.5 g 1% Pt/C (separated from example 22): 0.067 g Triphenyl phosphine: 0.08165

P-toluene sulphonic acid: 1.065 g

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 400 h$^{-1}$ and 98% conversion of p-IBPE with ibuprofen selective of 99%. The catalyst was filtered out, the solvent evaporated and the reaction mixture re-dissolved in toluene. The solid portion, which is a mixture of LiCl and lithium slat of p-toluene sulphonic acid, was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation vacuum distillation gives the pure product.

EXAMPLE 24

A 50 ml stirred autoclave was charged with the following reactants 1-(4'-isobutylphenyl)ethanol: 2.5g 1% Pt/C (separated from example 23) 0.04 g Triphenyl phosphine: 0.081665 g P-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 380 h.$^{-1}$ and 99% conversion of p-IBPE with ibuprofen selectivity of 99.3%. The catalyst was filtered out, the solvent evaporated and the reaction mixture re-dissolved in toluene. The solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation and vacuum distillation gives the pure product.

EXAMPLE 25

A 50 ml stirred autoclave was charged with the following reactants.

Sec. phenylethyl alcohol: 2.5 g

1% Pd/C: 0.1 g triphenyl phosphine: 0.08165 g p-toluene sulphonic acid: 1.065 g

LiCl: 0.2365 g

H$_2$O: 1.7 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was the cooled and the liquid phase analysed by gas chromatography.

The GC analysis showed TOF 310 h$^{-1}$ and 99% conversion of sec. phenethyl alcohol with 2-phenyl propionic acid selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane, evaporation and vacuum distillation gives the pure product.

EXAMPLE 26

A 50 ml stirred autoclave was charged with the following reactants 1-(6 methoxy-2-naphthyl)ethanol: 1 g
1% Pd/C: 0.1 g
triphenyl phosphine: 0.08165g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reaction was then cooled and the liquid phase analysed by gas chromatography.

The GC analysis showed TOF of 300 h-1 and 99% conversion of 1-(6-methoxy-2-naphthyl)ethanol with naproxen selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with a saturated solution of sodium bicarbonate two–three times and the aqueous phase is separated to obtain the sodium salt of naproxen.

EXAMPLE 27

A 50 ml stirred autoclave was charged with the following reactants 1-(4'-isobutylphenyl)ethanol: 2.5 g
1% Pd/ZSM5: 0.1 g
triphenyl phosphine: 0.08165 g
p-toluenyl sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until pressure drop was too low. The reactor was then cooled and the liquid phase analysed by gas chromatography.

The GC analysis showed TOF of 410 $h^{-1}$ and 96% conversion of p-IBPE with ibuprofen selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane, evaporation and vacuum distillation gives the pure product.

EXAMPLE 28

A 50 ml stirred autoclave was charged with the following reactants 1-(4'-isobutylphenyl)ethanol: 2.5 g
1% Pd/γ-alumina: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 450 $h^{-1}$ and 98% conversion of p-IBPE with ibuprofen selectivity of 97.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 29

A 50 ml stirred autoclave was charged with the following reactants 1-(4'-isobutylphenyl)ethanol: 2.5 g
Pd metal powder: 5 mg
Triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analysed by gas chromatography.

The GC analysis showed TOF of 120 $h^{-1}$ and 98% conversion of p-IBPE with ibuprofen selectivity of 86%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two three times and the aqueous phase is separated to obtain the sodium salt of ibuprofen, which on hydrolysis with acid and extraction with dichloromethane, evaporation and vacuum distillation gives the pure product.

EXAMPLE 30

A 50 ml stirred autoclave was charged with the following reactants 1-(4'-isobutylphenyl)ethanol: 2.5 g
Pd metal powder: 0.005 g
Triphenyl phosphine: 0.049 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 85 $h^{-1}$ and 98% conversion of p-IBPE with ibuprofen selectivity of 98.5%. The catalyst was filtered out and the solvent evaporated and the reaction mixture re-dissolved in the toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 31

A 50 ml stirred autoclave was charged with the following reactants.

1-(4'-isobutylphenyl)ethanol: 2.5 g
Pd metal powder: 0.005 g
Triphenyl phosphine: 0.049 g
10% HCE: 6 ml
Methyl ethyl ketone: 19 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 20 $h^{-1}$ and 98% conversion of p-IBPE with ibuprofen selectivity of 96%. The catalyst was filtered out and the solvent evaporated and the reaction mixture re-dissolved in toluene. The filtrate is treated with saturated solution of sodium bicarbonate two– three times and the aqueous phase is separated to obtain the sodium salt of ibuprofen, which on hydrolysis with acid and extraction with dichloromethane gives the pure product.

EXAMPLE 32

A 50 ml stirred autoclave was charged with the following reactants 1-(4'-isobutylphenyl)ethanol: 2.5 g
1% Pd/C: 0.1 g
triphenyl phosphine: 0.08165 g
50% HCl: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 320 $h^{-1}$ and 98% conversion of p-IBPE with ibuprofen selectivity of 98.7%. The catalyst was filtered out and the solvent evaporated and the reaction mixture re-dissolved in toluene. The filtrate is treated with saturated solution of sodium bicarbonate two– three times and the aqueous phase is separated to obtain the sodium salt of ibuprofen, which on hydrolysis with acid and extraction with dichloromethane gives the pure product.

EXAMPLE 33

A 50 ml stirred autoclave was charged with the following reactants 1-(4'-isobutylphenyl)ethanol: 2.5 g
1% Pd/C: 0.1 g
triphenyl phosphine: 0.08165 g
p-toluene sulphonic acid: 0.5325 g
LiCl: 0.1183 g
$H_2O$: 1.2 ml
Methyl ethyl ketone 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, string started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 500 $h^{-1}$ and 98% conversion of p-IBPE with ibuprofen selectivity of 97.7%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 34

A 50 ml stirred autoclave was charged with the following reactants 1-(4'-isobutylphenyl)ethanol: 2.5 g 1% Pd/C: 0.1 g triphenyl phosphine: 0.08165 g p-toluene sulphonic acid: 1.065 g LiCl: 0.2365 g $H_2O$: 1.2 ml Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 $h^{-1}$ and 97% conversion of p-IBPE with ibuprofen selectivity of 97.7%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 35

The procedure of Example 19 was followed except that instead of 1-(4'-isobutyl phenyl)ethanol, 1-(4'-isobutyl phenyl)ethyl chloride and instead of toluene, methyl ethyl ketone was employed in the same amount.

The GC analysis showed TOF of 800 $h^{-1}$ and 99% conversion of 1-(4'-isobutyl phenyl)ethyl chloride with ibuprofen selectivity of 98.5%. Pure product was extracted in accordance with the procedure contained in Example 19.

EXAMPLE 36

The procedure of Example 35 was followed except that 1% Pd/C (separated from Example 35) was employed in an amount of 0.061 g and instead of toluene, methyl ethyl ketone was employed in the same amount.

The GC analysis showed TOF of 810 $h^{-1}$ and 98% conversion of 1-(4'-isobutyl phenyl)ethyl chloride with ibuprofen selectivity of 98%. Pure product was extracted in accordance with the procedure contained in Example 35.

EXAMPLE 37

The procedure of Example 36 was followed except that 1% Pd/C (separated from Example 36) was employed in an amount of 0.045 g and instead of toluene, methyl ethyl ketone was employed in the same amount.

The GC analysis showed TOF of 790 $h^{-1}$ and 99% conversion of 1-(4'-isobutyl phenyl)ethyl chloride with ibuprofen selectivity of 98%. Pure product was extracted in accordance with the procedure contained in Example 36.

EXAMPLE 38

The procedure of Example 36 was followed except that instead of 1% Pd/C, 1% Pt/C was employed in an amount of 0.1 g and instead of toluene, methyl ethyl ketone was employed in the same amount.

The GC analysis showed TOF of 400 $h^{-1}$ and 99% conversion of 1-(4'-isobutyl phenyl)ethyl chloride with ibuprofen selectivity of 99.2%. The catalyst was separated out and pure product was extracted in accordance with the procedure contained in Example 36.

EXAMPLE 39

The procedure of Example 38 was followed except that 1% Pd/C separated from Example 38 was used in an amount of 0.065 g and instead of toluene, methyl ethyl ketone was employed in the same amount.

The GC analysis showed TOF of 410 $h^{-1}$ and 98% conversion of 1-(4'-isobutyl phenyl)ethyl chloride with ibuprofen selectivity of 99%. The catalyst was separated out and pure product was extracted in accordance with the procedure contained in Example 38.

EXAMPLE 40

The procedure of Example 39 was followed except that 1% Pd/C separated from Example 36 was used in an amount of 0.043 g and instead of toluene, methyl ethyl ketone was employed in the same amount.

The GC analysis showed TOF of 390 $h^{-1}$ and 99% conversion of 1-(4'-isobutyl phenyl)ethyl chloride with ibuprofen selectivity of 99%. The catalyst was separated out and pure product was extracted in accordance with the procedure contained in Example 39.

EXAMPLE 41

The procedure of Example 35 was followed except that instead of 1-(4'-isobutyl phenyl)ethyl chloride, 1-phenyl ethyl chloride was employed in the same amount and instead of toluene, methyl ethyl ketone was employed in the same amount.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 99% conversion of 1-phenyl ethyl chloride with ibuprofen selectivity of 97.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 42

A 50 ml stirred autoclave was charged with the following reactants 1-(6-methoxy-2-naphthyl)ethyl chloride: 1 g 1% Pd/C: 0.1 g triphenyl phosphine: 0.08165 g p-toluene sulphonic acid: 0.51 g LiCl: 0.1 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 130 h$^{-1}$ and 98% conversion of 6-methoxy naphthyl ethanol with naproxen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated which on hydrolysis and extraction with dichloromethane gives the pure product.

EXAMPLE 43

A 50 ml stirred autoclave was charged with the following reactants 1-(4'-isobutylphenyl)ethyl chloride: 2.5 g 1% Pd/ZSM 5: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 h$^{-1}$ and 96% conversion of 1-(4'-isobutylphenyl)ethyl chloride with ibuprofen selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 44

A 50 ml stirred autoclave was charged with the following reactants 1-(4'-isobutylphenyl)ethyl chloride: 2.5 g 1% Pd/γ-Alumina: 0.1 g triphenyl phosphine: 0.08165 g p-toluene sulphonic acid: 1.065 g LiCl: 0.2365 g H$_2$O: 1.2 ml Methyl ethyl ketone: 21. 5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 350 h$^{-1}$ and 98% conversion of 1-(4'-isobutylphenyl)ethyl chloride with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 45

A 50 ml stirred autoclave was charged with the following reactants 1-(4'-isobutylphenyl)ethyl chloride: 2.5 g Pd metal powder: 5 mg triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 h$^{-1}$ and 98% conversion of 1-(4'-isobutylphenyl)ethyl chloride with ibuprofen selectivity of 84%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 46

A 50 ml stirred autoclave was charged with the following reactants 1-(4'-isobutylphenyl)ethyl chloride: 2.5 g Pd metal powder: 0.005 g triphenyl phosphine: 0.049 g 10% HCl: 6 ml Methyl ethyl ketone: 19 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 22 $h^{-1}$ and 98% conversion of 1-(4'-isobutylphenyl)ethyl chloride with ibuprofen selectivity of 95.6%. The catalyst was filtered out and the solvent evaporated and the reaction mixture re-dissolved in toluene. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 47

A 50 ml stirred autoclave was charged with the following reactants 1-(4-isobutylphenyl)ethyl chloride: 2.5 g 1% Pd/C: 0.1 g triphenyl phosphine: 0.08165 g 50% HCl: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 340 $h^{-1}$ and 98% conversion of 1-(4'-isobutylphenyl)ethyl chloride with ibuprofen selectivity of 98.5%. The catalyst was filtered out and the solvent evaporated and the reaction mixture re-dissolved in toluene. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 48

A 50 ml stirred autoclave was charged with the following reactants 1-(4'-isobutylphenyl)ethyl chloride: 2.5 g 1% Pd/C: 0.1 g triphenyl phosphine: 0.08165 g p-toluene sulphonic acid: 0.532 g LiCl: 0.1183 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 260 $h^{-1}$ and 98% conversion of 1-(4'-isobutylphenyl)ethyl chloride with ibuprofen selectivity of 98.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 49

A 50 ml stirred autoclave was charged with the following reactants 1-(4'-isobutylphenyl)ethyl chloride: 2.5 g 1% Pd/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 120 $h^{-1}$ and 97% conversion of 1-(4'-isobutylphenyl)ethyl chloride with ibuprofen selectivity of 98.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 50

A 50 ml stirred autoclave was charged with the following reactants

Styrene: 2.5 g

1% Pd/C: 0.1 g triphenyl phosphine: 0.08165 g p-toluene sulphonic acid: 1.065 g

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 800 h$^{-1}$ and 99% conversion of styrene with 2-aryl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 51

A 50 ml stirred autoclave was charged with the following reactants

Styrene: 2.5 g

1% Pd/C (separated from Example 50): 0.056 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 820 h$^{-1}$ and 98% conversion of styrene with 2-phenyl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 52

A 50 ml stirred autoclave was charged with the following reactants

Styrene: 2.5 g

1% Pd/C (separated from Example 51): 0.049 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 780 h$^{-1}$ and 99% conversion of styrene with 2-phenyl propionic acid selectivity of 98.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 53

A 50 ml stirred autoclave was charged with the following reactants

Styrene: 2.5 g

1% Pt/C: 0.1 g triphenyl phosphine: 0.08165 g p-toluene sulphonic acid: 1.065 g

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 400 h$^{-1}$ and 99% conversion of styrene with 2-phenyl propionic acid selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 54

A 50 ml stirred autoclave was charged with the following reactants

Styrene: 2.5 g
1% Pt/C (separated from Example 53): 0.067 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 410 $h^{-1}$ and 98% conversion of styrene with 2-phenyl propionic acid selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 55

A 50 ml stirred autoclave was charged with the following reactants

Styrene: 2.5 g
1% Pt/C (separated from Example 54): 0.041 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 $h^{-1}$ and 99% conversion of styrene with 2-phenyl propionic acid selectivity of 99.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 56

A 50 ml stirred autoclave was charged with the following reactants 4-isobutyl styrene: 2.5 g
1% Pd/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 710 $h^{-1}$ and 99% conversion of 4-isobutylstyrene with ibuprofen selectivity of 97%. The catalyst was filtered out and the solvent evaporated and the reaction mixture redissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 57

A 50 ml stirred autoclave was charged with the following reactants 4-isobutyl styrene: 2.5 g
1% Pt/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 410 $h^{-1}$ and 99% conversion of 4-isobutyl styrene with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of ibuprofen, which on hydrolysis with acid and extraction with dichloromethane gives the pure product.

EXAMPLE 58

A 50 ml stirred autoclave was charged with the following reactants 4-tert.butylstyrene: 2.5 g 1% Pd/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-(4'-tert.butylphenyl)propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 510 $h^{-1}$ and 99% conversion of 4-tert.butylstyrene with 2-(4'-tert.butylphenyl)propionic acid selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-(4'-tert.butylphenyl)propionic acid, which on hydrolysis with acid and extraction with dichloromethane gives the pure product.

EXAMPLE 59

A 50 ml stirred autoclave was charged with the following reactants

Styrene: 2.5 g

1% Pd/ZSM 5: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop, and by liquid sampling. The reaction was continued until the pressure drop was too low. The reactor was then cooled and the liquid phase analyzed by gas chromatography.

The GC analysis showed TOF of 390 $h^{-1}$ and 96% conversion of styrene with 2-phenyl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 60

A 50 ml stirred autoclave was charged with the following reactants

Styrene: 2.5 g

1% Pd/γ-Alumina: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 430 $h^{-1}$ and 98% conversion of styrene with 2-phenyl propionic acid selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 61

A 50 ml stirred autoclave was charged with the following reactants

Styrene: 2.5 g

Pd metal powder: 5 mg triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 180 $h^{-1}$ and 98% conversion of styrene with 2-phenyl propionic acid selectivity of 87%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 62

A 50 ml stirred autoclave was charged with the following reactants

Styrene: 2.5 g
Pd metal powder: 0.005 g
triphenyl phosphine: 0.049 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 80 $h^{-1}$ and 98% conversion of styrene with 2-phenyl propionic acid selectivity of 98.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 63

A 50 ml stirred autoclave was charged with the following reactants

Styrene: 2.5 g
Pd metal powder: 0.005 g
triphenyl phosphine: 0.049 g
10% HCl: 6 ml
Methyl ethyl ketone: 19 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 24 $h^{-1}$ and 98% conversion of styrene with 2-phenyl propionic acid selectivity of 96%. The catalyst was filtered out and the solvent evaporated and the reaction mixture re-dissolved in toluene. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 64

A 50 ml stirred autoclave was charged with the following reactants

Styrene: 2.5 g
1% Pd/C: 0.1 g
triphenyl phosphine: 0.08165 g
50% HCl: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 98% conversion of styrene with 2-phenyl propionic acid selectivity of 98.7%. The catalyst was filtered out and the solvent evaporated and the reaction mixture re-dissolved in toluene. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 65

A 50 ml stirred autoclave was charged with the following reactants

Styrene: 2.5 g
1% Pd: 0.1 g
triphenyl phosphine: 0.05 g
p-toluene sulphonic acid: 1.065 g
LiCl: 0.2365 g H$_2$O: 1.2 ml Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 2900 h$^{-1}$ and 98% conversion of styrene with 2-phenyl propionic acid selectivity of 97.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate is treated with saturated solution of sodium bicarbonate two–three times and the aqueous phase is separated to obtain the sodium salt of 2-phenyl propionic acid, which on hydrolysis with acid and extraction with dichloromethane gives the pure product.

EXAMPLE 66

A 50 ml stirred autoclave was charged with the following reactants

Styrene: 2.5 g

1% Rh/C: 0.1 g triphenyl phosphine: 0.08165 g p-toluene sulphonic acid: 1.065 g

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 420 h$^{-1}$ and 99.5% conversion of styrene with 2-phenyl propionic acid selectivity of 98.4%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 67

A 50 ml stirred autoclave was charged with the following reactants

Styrene: 2.5 g

1% Rh/C (separated from Example 66): 0.056 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 h$^{-1}$ and 98%conversion of styrene with 2-phenyl propionic id selectivity of 98.5%. The catalyst was filtered out and the solvent evaporate d and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 68

A 50 ml stirred autoclave was charged with the following reactants

Styrene: 2.5 g

1% Rh/C (separated from Example 67): 0.042 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 h$^{-1}$ and 99% conversion of styrene with 2-phenyl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out.

The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 69

A 50 ml stirred autoclave was charged with the following reactants 4-isobutyl styrene: 2.5 g
1% Rh/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography. The GC analysis showed TOF of 420 $h^{-1}$ and 98% conversion of 4-isobutyl styrene with ibuprofen selectivity of 98.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 70

A 50 ml stirred autoclave was charged with the following reactants 1-(6-methoxy-2-naphthyl)ethene: 2.5 g
1% Rh/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 120 $h^{-1}$ and 98% conversion of 1-(6-methoxy-2-naphthyl)ethene with naproxen selectivity of 98.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of naproxen, which on hydrolysis with acid and extraction with dichloromethane, evaporation and vacuum distillation gives the pure product.

EXAMPLE 71

A 50 ml stirred autoclave was charged with the following reactants 4-tert.butyl styrene: 2.5 g
1% Rh/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-(4'-tert.butylphenyl)propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 400 $h^{-1}$ and 96% conversion of 4-tert.butyl styrene with 2-(4'-tert.butylphenyl)propionic acid selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-(4'-tert.butylphenyl)propionic acid, which on hydrolysis with acid and extraction with dichloromethane, evaporation and vacuum distillation gives the pure product.

EXAMPLE 72

A 50 ml stirred autoclave was charged with the following reactants

Styrene: 2.5 g
1% Rh/ZSM 5: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 340 h$^{-1}$ and 96% conversion of styrene with 2-phenyl propionic acid selectivity of 96%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 73

A 50 ml stirred autoclave was charged with the following reactants

Styrene: 2.5 g

1% Rh/γ-Alumina: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 h$^{-1}$ and 98% conversion of styrene with 2-phenyl propionic acid selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 74

A 50 ml stirred autoclave was charged with the following reactants

Styrene: 2.5 g

1% Rh/C: 0.1 g triphenyl phosphine: 0.08165 g

50% HCl: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 350 h$^{-1}$ and 98% conversion of styrene with 2-phenyl propionic acid selectivity of 98.9%. The catalyst was filtered out and the solvent evaporated and the reaction mixture re-dissolved in toluene. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 75

A 50 ml stirred autoclave was charged with the following reactants

Styrene: 2.5 g

1% Rh/C: 0.1 g triphenyl phosphine: 0.08165 g p-toluene sulphonic acid: 1.065 g

LiCl: 0.2365 g

H$_2$O: 1.2 ml

Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 150 h$^{-1}$ and 97% conversion of styrene with 2-phenyl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 76

A 50 ml stirred autoclave was charged with the following reactants

Styrene: 2.5 g

1% Ir/C: 0.1 g triphenyl phosphine: 0.08165 g p-toluene sulphonic acid: 1.065 g

LiCl: 0.2365 g $H_2O$: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 $h^{-1}$ and 98% conversion of styrene with 2-phenyl propionic acid selectivity of 98.2%. The catalyst was filtered out and the solvent evaporated and the reaction mixture redissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 77

A 50 ml stirred autoclave was charged with the following reactants

Styrene: 2.5 g

1% Ir/C (separated from Example 76): 0.056 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 98% conversion of styrene with 2-phenyl propionic acid selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 78

A 50 ml stirred autoclave was charged with the following reactants

Styrene: 2.5 g

1% Ir/C (separated from Example 77): 0.048 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 $h^{-1}$ and 99% conversion of styrene with 2-phenyl propionic acid selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 79

A 50 ml stirred autoclave was charged with the following reactants

Styrene: 2.5 g

1% Ru/C: 0.1 g triphenyl phosphine: 0.08165 g p-toluene sulphonic acid: 1.065 g

LiCl: 0.2365 g $H_2O$: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 470 $h^{-1}$ and 99% conversion of styrene with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 80

A 50 ml stirred autoclave was charged with the following reactants

Styrene: 2.5 g
1% Ru/C (separated from Example 79): 0.076 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 99% conversion of styrene with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 81

A 50 ml stirred autoclave was charged with the following reactants

Styrene: 2.5 g
1% Ru/C (separated from Example 80): 0.040 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 $h^{-1}$ and 99% conversion of styrene with ibuprofen selectivity of 99.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 82

A 50 ml stirred autoclave was charged with the following reactants

Styrene: 2.5 g
1% Ni/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 300 $h^{-1}$ and 99% conversion of styrene with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 83

A 50 ml stirred autoclave was charged with the following reactants

Styrene: 2.5 g
1% Ni/C (separated from Example 82): 0.067 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 h$^{-1}$ and 98% conversion of styrene with 2-phenyl propionic acid selectivity of 99.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 84

A 50 ml stirred autoclave was charged with the following reactants

Styrene: 2.5 g

1% Ni/C (separated from Example 83): 0.04 g triphenyl phosphine: 0.08165 g p-toluene sulphonic acid: 1.065 g LiCl : 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 308 h$^{-1}$ and 99% conversion of styrene with 2-phenyl propionic acid selectivity of 99.1%. The catalyst was filtered out and the solvent evaporated and the reaction mixture redissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 85

A 50 ml stirred autoclave was charged with the following reactants

Styrene: 2.5 g

1% Co/C: 0.1 g triphenyl phosphine: 0.08165 g p-toluene sulphonic acid: 1.065 g

LiCl: 0.2365 g

H$_2$O: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 245 h$^{-1}$ and 99% conversion of styrene with 2-phenyl propionic acid selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 86

A 50 ml stirred autoclave was charged with the following reactants

Styrene: 2.5 g

1% Co/C (separated from Example 85): 0.069 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 250 h$^{-1}$ and 98% conversion of styrene with 2-phenyl propionic acid selectivity of 99.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 87

A 50 ml stirred autoclave was charged with the following reactants 4-isobutyl styrene: 2.5 g 1% Ni/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 270 $h^{-1}$ and 99% conversion of 4-isobutyl styrene with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 88

A 50 ml stirred autoclave was charged with the following reactants 4-isobutyl styrene: 2.5 g 1% Co/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 290 $h^{-1}$ and 99% conversion of 4-isobutyl styrene with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 89

A 50 ml stirred autoclave was charged with the following reactants 4-isobutyl styrene: 2.5 g 1% Ru/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 $h^{-1}$ and 99% conversion of 4-isobutyl styrene with ibuprofen selectivity of 98.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 90

A 50 ml stirred autoclave was charged with the following reactants 4-tertbutyl styrene: 2.5 g 1% Ru/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-(4-tert.butylphenyl)propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 330 $h^{-1}$ and 99% conversion of 4-tert.butyl styrene with 2-(4-tert.butylphenyl)propionic acid selectivity of 98.9%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated, which on hydrolysis and extraction with dichloromethane, evaporation and vacuum distillation gives the pure product.

EXAMPLE 91

A 50 ml stirred autoclave was charged with the following reactants

Styrene: 2.5 g

1% Ni/ZSM 5: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 210 $h^{-1}$ and 96% conversion of styrene with 2-phenyl propionic acid selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 92

A 50 ml stirred autoclave was charged with the following reactants

Styrene: 2.5 g

1% Ru/γ-Alumina: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 280 $h^{-1}$ and 98% conversion of styrene with 2-phenyl propionic acid selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 93

A 50 ml stirred autoclave was charged with the following reactants

Styrene: 2.5 g

1% Ni/C: 0.1 g triphenyl phosphine: 0.08165 g

50% HCl: 1.2 ml

Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 220 $h^{-1}$ and 98% conversion of styrene with 2-phenyl propionic acid selectivity of 98.7%. The catalyst was filtered out and the solvent evaporated and the reaction mixture re-dissolved in toluene. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 94

A 50 ml stirred autoclave was charged with the following reactants

Styrene: 2.5 g

1% Ni/C: 0.1 g triphenyl phosphine: 0.08165 g p-toluene sulphonic acid: 1.065 g

LiCl: 0.2365 g $H_2O$: 1.2 ml

Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 h$^{-1}$ and 97% conversion of styrene with 2-phenyl propionic acid selectivity of 99.2%. The catalyst was filtered out and the solvent evaporated and the reaction mixture re-dissolved in toluene. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 95

A 50 ml stirred autoclave was charged with the following reactants 1-(4'-isobutylphenyl)ethyl chloride: 2.5 g 1% Ru/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 480 h$^{-1}$ and 99% conversion of 1-(4'-isobutylphenyl)ethyl chloride with ibuprofen selectivity of 99.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 96

A 50 ml stirred autoclave was charged with the following reactants 1-(4'-isobutylphenyl)ethyl chloride: 2.5 g 1% Ru/C (separated form Example 95): 0.066 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 h$^{-1}$ and 99% conversion of 1-(4'-isobutylphenyl)ethyl chloride with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 97

A 50 ml stirred autoclave was charged with the following reactants 1-(4'-isobutylphenyl)ethyl chloride: 2.5 g 1% Ru/C (separated from Example 96): 0.050 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 350 h$^{-1}$ and 99% conversion of 1-(4'-isobutylphenyl)ethyl chloride with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 98

A 50 ml stirred autoclave was charged with the following reactants 1-(4'-isobutylphenyl)ethyl chloride: 2.5 g 1% Ni/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 h$^{-1}$ and 99% conversion of 1-(4'-isobutylphenyl)ethyl chloride with ibuprofen selectivity of 99.4%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 99

A 50 ml stirred autoclave was charged with the following reactants 1-(4'-isobutylphenyl)ethyl chloride: 2.5 g 1% Ni/C (separated from Example 98): 0.07 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 330 h$^{-1}$ and 98% conversion of 1-(4'-isobutylphenyl)ethyl chloride with ibuprofen selectivity of 99.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 100

A 50 ml stirred autoclave was charged with the following reactants 1-(4'-isobutylphenyl)ethyl chloride: 2.5 g 1% Ni/C (separated from Example 99): 0.05 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 h$^{-1}$ and 99% conversion of 1-(4'-isobutylphenyl)ethyl chloride with ibuprofen selectivity of 99.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 101

A 50 ml stirred autoclave was charged with the following reactants 1-(4'-isobutylphenyl)ethyl chloride: 2.5 g 1% Co/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pre drop and by liquid sampling. The reaction was continued until the pressure drop was too low. The reactor was then cooled and the liquid phase analyzed by gas chromatography.

The GC analysis showed TOF 70 h$^{-1}$ and 99% conversion of 1-(4'-isobutylphenyl)ethyl chloride with ibuprofen selectivity 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 102

A 50 ml stirred autoclave was charged with the following reactants 1-(4'-isobutylphenyl)ethyl chloride: 2.5 g 1% Co/C (separated from Example 101): 0.065 g triphenyl phosphine: 0.08165 g p-toluene sulphonic acid: 1.065 g LiCl: 0.2365 g $H_2O$: 1.2 ml Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 260 $h^{-1}$ and 98% conversion of 1-(4'-isobutylphenyl)ethyl chloride with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 103

A 50 ml stirred autoclave was charged with the following reactants 1-phenyl ethyl chloride: 2.5 g 1% Ni/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 270 $h^{-1}$ and 99% conversion of 1-phenyl ethyl chloride with 2-phenyl propionic acid selectivity of 98.6%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 104

A 50 ml stirred autoclave was charged with the following reactants 1-(6-methoxy-2-naphthyl)ethyl chloride: 1 g 1% Ru/C: 0.1 g triphenyl phosphine: 0.08165 g p-toluene sulphonic acid: 0.5 g LiCl: 0.1 g $H_2O$: 1.2 ml Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 120 $h^{-1}$ and 99% conversion of 1-(6-methoxy-2-naphthyl)ethyl chloride with naproxen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated, which on hydrolysis and extraction with dichloromethane gives the pure product.

EXAMPLE 105

A 50 ml stirred autoclave was charged with the following reactants 1-(4'-isobutylphenyl)ethyl chloride: 2.5 g 1% Ni/ZSM5: 0.1 g triphenyl phosphine: 0.08165 g p-toluene sulphonic acid: 1.065 g LiCl: 0.2365 g $H_2O$: 1.2 ml Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 250 h$^{-1}$ and 96% conversion of 1-(4'-isobutylphenyl)ethyl chloride with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 106

A 50 ml stirred autoclave was charged with the following reactants 1-(4'-isobutylphenyl)ethyl chloride: 2.5 g 1% Ru/γ-Alumina: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 300 h$^{-1}$ and 98% conversion of 1-(4'-isobutylphenyl)ethyl chloride with ibuprofen selectivity of 98.9%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 107

A 50 ml stirred autoclave was charged with the following reactants 1-(4'-isobutylphenyl)ethyl chloride: 2.5 g 1% Ni/C: 0.1 g triphenyl phosphine: 0.08165 g 50% HCl: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 250 h$^{-1}$ and 98% conversion of 1-(4'-isobutylphenyl)ethyl chloride with ibuprofen selectivity of 99%. The catalyst was filtered out and the solvent evaporated and the reaction mixture re-dissolved in toluene. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 108

A 50 ml stirred autoclave was charged with the following reactants 1-4'-isobutylphenyl)ethyl chloride: 2.5 g 1% Ni/C: 0.1 g triphenyl phosphine: 0.08165 g p-toluene sulphonic acid: 1.065 g LiCl: 0.2365 g $H_2O$: 1.2 ml Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 80 h$^{-1}$ and 97% conversion of 1-(4'-isobutylphenyl)ethyl chloride with ibuprofen selectivity of 99.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 109

A 50 ml stirred autoclave was charged with the following reactants 1-(4'-isobutylphenyl)ethanol: 2.5 g 1% Ru/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 470 $h^{-1}$ and 99% conversion of p-IBPE with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 110

A 50 ml stirred autoclave was charged with the following reactants 1-(4'-isobutylphenyl)ethanol: 2.5 g 1% Ru/C (separated from Example 109): 0.076 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 99% conversion of p-IBPE with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 111

A 50 ml stirred autoclave was charged with the following reactants 1-(4'-isobutylphenyl)ethanol: 2.5 g 1% Ru/C (separated from Example 110): 0.040 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 $h^{-1}$ and 99% conversion of p-IBPE with ibuprofen selectivity of 99.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 112

A 50 ml stirred autoclave was charged with the following reactants 1-(4'-isobutylphenyl)ethanol: 2.5 g 1% Ni/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 300 $h^{-1}$ and 99% conversion of p-IBPE with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 113

A 50 ml stirred autoclave was charged with the following reactants 1-(4'-isobutylphenyl)ethanol: 2.5 g 1% Ni/C (separated from Example 112): 0.067 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 h$^{-1}$ and 98% conversion of p-IBPE with ibuprofen selectivity of 99.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 114

A 50 ml stirred autoclave was charged with the following reactants 1-(4'-isobutylphenyl)ethanol: 2.5 g 1% Ni/C (separated from Example 113): 0.04 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 308 h$^{-1}$ and 99% conversion of p-IBPE with ibuprofen selectivity of 99.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 115

A 50 ml stirred autoclave was charged with the following reactants 1-(4'-isobutylphenyl)ethanol: 2.5 g 1% Co/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 245 h$^{-1}$ and 99% conversion of p-IBPE with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 116

A 50 ml stirred autoclave was charged with the following reactants 1-(4'-isobutylphenyl)ethanol: 2.5 g 1% Co/C (separated from Example 115): 0.069 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 250 h$^{-1}$ and 98% conversion of p-IBPE with ibuprofen selectivity of 99.3%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 117

A 50 ml stirred autoclave was charged with the following reactants

Sec. phenylethyl alcohol: 2.5 g
1% Ni/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 170 $h^{-1}$ and 99% conversion of sec.phenethyl alcohol with 2-phenyl propionic acid selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 118

A 50 ml stirred autoclave was charged with the following reactants 1-(6-methoxy-2-naphthyl)ethanol: 1 g
1% Ru/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 130 $h^{-1}$ and 99% conversion of 6 methoxy naphthyl ethanol with naproxen selectivity of 98.9%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated, which on hydrolysis and extraction with dichloromethane gives the pure product.

EXAMPLE 119

A 50 ml stirred autoclave was charged with the following reactants 1-(4'-isobutylphenyl)ethanol: 2.5 g
1% Ni/ZSM 5: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 210 $h^{-1}$ and 96% conversion of p-IBPE with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 120

A 50 ml stirred autoclave was charged with the following reactants 1-(4'-isobutylphenyl)ethanol: 2.5 g
1% Ru/γ-Alumina: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 280 h$^{-1}$ and 98% conversion of p-IBPE with ibuprofen selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 121

A 50 ml stirred autoclave was charged with the following reactants 1-4'-isobutylphenyl)ethanol: 2.5 g
1% Ni/C: 0.1 g
triphenyl phosphine: 0.08165 g
50% HCl: 1.2 ml
Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 220 h$^{-1}$ and 98% conversion of p-IBPE with ibuprofen selectivity of 98.7%. The catalyst was filtered out and the solvent evaporated and the reaction mixture re-dissolved in toluene. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 122

A 50 ml stirred autoclave was charged with the following reactants 1-(4'-isobutylphenyl)ethanol: 2.5 g
1% Ni/C: 0.1 g
triphenyl phosphine: 0.08165 g
p-toluene sulphonic acid: 1.065 g
LiCl: 0.2365 g
H$_2$O: 1.2 ml
Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 h$^{-1}$ and 97% conversion of p-IBPE with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 123

A 50 ml stirred autoclave was charged with the following reactants 1-(4'-isobutylphenyl)ethanol: 2.5 g
1% Rh/C: 0.1 g
triphenyl phosphine: 0.08165 g
p-toluene sulphonic acid: 1.065 g
LiCl: 0.2365 g
H$_2$O: 1.2 ml
Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 400 h$^{-1}$ and 99.5% conversion of p-IBPE with ibuprofen selectivity of 98.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 124

A 50 ml stirred autoclave was charged with the following reactants 1-(4'-isobutylphenyl)ethanol: 2.5 g
1% Rh/C (separated from Example 123): 0.056 g
triphenyl phosphine: 0.08165 g
p-toluene sulphonic acid: 1.065 g
LiCl: 0.2365 g
H$_2$O: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 $h^{-1}$ and 98% conversion of p-IBPE with ibuprofen selectivity of 98.1%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 125

A 50 ml stirred autoclave was charged with the following reactants 1-(4'-isobutylphenyl)ethanol: 2.5 g
1% Rh/C (separated from Example 124): 0.042 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 $h^{-1}$ and 99% conversion of p-IBPE with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 126

A 50 ml stirred autoclave was charged with the following reactants

Sec. phenylethyl alcohol: 2.5 g
1% Rh/C: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 220 $h^{-1}$ and 98% conversion of sec.phenethyl alcohol with 2-phenyl propionic acid selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 127

A 50 ml stirred autoclave was charged with the following reactants 1-(6-methoxy-2-naphthyl)ethanol: 1 g
1% Rh/C: 0.1 g
triphenyl phosphine: 0.08165 g
p-toluene sulphonic acid: 0.5 g
LiCl: 0.1 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 $h^{-1}$ and 96% conversion of 6 methoxy naphthyl ethanol with naproxen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated, which on hydrolysis and extraction with dichloromethane gives the pure product.

EXAMPLE 128

A 50 ml stirred autoclave was charged with the following reactants 1-(4'-isobutylphenyl)ethanol: 2.5 g
1% Rh/ZSM 5: 0.1 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 310 $h^{-1}$ and 96% conversion of p-IBPE with ibuprofen selectivity of 97%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 129

A 50 ml stirred autoclave was charged with the following reactants 1-(4'-isobutylphenyl)ethanol: 2.5 g
 1% Rh/γ-Alumina: 0.1 g
 triphenyl phosphine: 0.08165 g
 p-toluene sulphonic acid: 1.065 g
 LiCl: 0.2365 g
 H$_2$O: 1.2 ml
 Methyl ethyl ketone: 21.5 ml.

The contents of the autoclave were flushed with nitrogen and then many times with carbon monoxide. Thereafter, the contents were heated to 1150° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 350 $h^{-1}$ and 98% conversion of p-IBPE with ibuprofen selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 130

A 50 ml stirred autoclave was charged with the following reactants 1-(4'-isobutylphenyl)ethanol: 2.5 g
 1% Rh/C: 0.1 g
 triphenyl phosphine: 0.08165 g
 50% HCl: 1.2 ml
 Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography. The GC analysis showed TOF of 320 $h^{-1}$ and 98% conversion of p-IBPE with ibuprofen selectivity of 98.7%. The catalyst was filtered out and the solvent evaporated and the reaction mixture re-dissolved in toluene. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 131

A 50 ml stirred autoclave was charged with the following reactants 1-(4'-isobutylphenyl)ethanol: 2.5 g
 1% Rh/C: 0.1 g
 triphenyl phosphine: 0.08165 g
 p-toluene sulphonic acid: 1.065 g
 LiCl: 0.2365 g
 H$_2$O: 1.2 ml
 Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 100 $h^{-1}$ and 97% conversion of p-IBPE with ibuprofen selectivity of 98.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 132

A 50 ml stirred autoclave was charged with the following reactants 1-(4'-isobutylphenyl)ethanol: 2.5 g
 1% Ir/C: 0.1 g
 triphenyl phosphine: 0.08165 g
 p-toluene sulphonic acid: 1.065 g
 LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 h$^{-1}$ and 99.5% conversion of p-IBPE with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 133

A 50 ml stirred autoclave was charged with the following reactants 1-(4'-isobutylphenyl)ethanol: 2.5 g 1% Ir/C (separated from Example 132): 0.056 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 390 h$^{-1}$ and 99% conversion of p-IBPE with ibuprofen selectivity of 98.4%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 134

A 50 ml stirred autoclave was charged with the following reactants 1-(4'-isobutylphenyl)ethanol: 2.5 g 1% Ir/C (separated from Example 133): 0.042 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 h$^{-1}$ and 99% conversion of p-IBPE with ibuprofen selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 135

A 50 ml stirred autoclave was charged with the following reactants 1-(4'-isobutylphenyl)ethyl chloride: 2.5 g 1% Rh/C: 0.1 g triphenyl phosphine: 0.08165 g p-toluene sulphonic acid: 1.065 g LiCl: 0.2365 g H$_2$O: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 450 h$^{-1}$ and 99% conversion of 1-(4'-isobutylphenyl)ethyl chloride with ibuprofen selectivity of 98.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 136

A 50 ml stirred autoclave was charged with the following reactants 1-(4'-isobutylphenyl)ethyl chloride: 2.5 g
1% Rh/C (separated from Example 135): 0.06 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 435 $h^{-1}$ and 98% conversion of 1-(4'-isobutylphenyl)ethyl chloride with ibuprofen selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 137

A 50 ml stirred autoclave was charged with the following reactants 1-(4'-isobutylphenyl)ethyl chloride: 2.5 g
1% Rh/C (separated from Example 136): 0.048 g
triphenyl phosphine: 0.08165 g
p-toluene sulphonic acid: 1.065 g
LiCl: 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 400 $h^{-1}$ and 99% conversion of 1-(4'-isobutylphenyl)ethyl chloride with ibuprofen selectivity of 98.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 138

A 50 ml stirred autoclave was charged with the following reactants 1-(4'-isobutylphenyl)ethyl chloride: 2.5 g
1% Ir/C: 0.1 g
triphenyl phosphine: 0.08165 g
p-toluene sulphonic acid: 1.065 g
LiCl : 0.2365 g
$H_2O$: 1.2 ml
Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 490 $h^{-1}$ and 99% conversion of 1-(4'-isobutylphenyl)ethyl chloride with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 139

A 50 ml stirred autoclave was charged with the following reactants 1-(4'-isobutylphenyl)ethyl chloride: 2.5 g
1% Ir/C (separated from Example 138): 0.067 g
triphenyl phosphine: 0.08165 g
p-toluene sulphonic acid: 1.065 g
LiCl: 0.2365 g
$H_2O$: 1.2 ml
Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 485 $h^{-1}$ and 98% conversion of 1-(4'-isobutylphenyl)ethyl chloride with ibuprofen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 140

A 50 ml stirred autoclave was charged with the following reactants 1-(4'-isobutylphenyl)ethyl chloride: 2.5 g 1% Ir/C (separated from Example 139): 0.046 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 470 $h^{-1}$ and 99% conversion of 1-(4'-isobutylphenyl)ethyl chloride with ibuprofen selectivity of 99.2%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 141

A 50 ml stirred autoclave was charged with the following reactants 1-phenyl ethyl chloride: 2.5 g 1% Rh/C: 0.1 g triphenyl phosphine: 0.08165 g p-toluene sulphonic acid 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of 2-phenyl propionic acid, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 400 $h^{-1}$ and 98% conversion of 1-phenyl ethyl chloride with 2-phenyl propionic acid selectivity of 98.8%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of 2-phenyl propionic acid, which on hydrolysis with acid and extraction with dichloromethane, evaporation and vacuum distillation gives the pure product.

EXAMPLE 142

A 50 ml stirred autoclave was charged with the following reactants 1-(6-methoxy-2-naphthyl)ethyl chloride: 2.5 g 1% Rh/C: 0.1 g triphenyl phosphine: 0.08165 g p-toluene sulphonic acid: 1.065 g LiCl: 0.2365 g $H_2O$: 1.2 ml Methyl ethyl ketone: 21.5 ml The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of naproxen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 150 $h^{-1}$ and 98% conversion of 1-(6-methoxy-2-naphthyl)ethyl chloride with naproxen selectivity of 99%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of naproxen, which on hydrolysis with acid and extraction with dichloromethane, evaporation and vacuum distillation gives the pure product.

EXAMPLE 143

A 50 ml stirred autoclave was charged with the following reactants 1-(4'-isobutylphenyl)ethyl chloride: 2.5 g 1% Rh/ZSM 5: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 370 $h^{-1}$ and 96% conversion of 1-(4'-isobutylphenyl)ethyl chloride with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 144

A 50 ml stirred autoclave was charged with the following reactants 1-(4'-isobutylphenyl)ethyl chloride: 2.5 g 1% Rh/γ-Alumina: 0.1 g triphenyl phosphine: 0.08165 g p-toluene sulphonic acid: 1.065 g LiCl: 0.2365 g $H_2O$: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 380 $h^{-1}$ and 98% conversion of 1-(4'-isobutylphenyl)ethyl chloride with ibuprofen selectivity of 98.5%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 145

A 50 ml stirred autoclave was charged with the following reactants 1-(4'-isobutylphenyl)ethyl chloride: 2.5 g 1% Rh/C: 0.1 g triphenyl phosphine: 0.08165 g 50% HCl: 1.2 ml Methyl ethyl ketone: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 330 $h^{-1}$ and 98% conversion of 1-(4'-isobutylphenyl)ethyl chloride with ibuprofen selectivity of 99%. The catalyst was filtered out and the solvent evaporated and the reaction mixture re-dissolved in toluene. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

EXAMPLE 146

A 50 ml stirred autoclave was charged with the following reactants 1-(4'-isobutylphenyl)ethyl chloride: 2.5 g 1% Rh/C: 0.1 g triphenyl phosphine: 0.08165 g p-toluene sulphonic acid: 1.065 g LiCl: 0.2365 g $H_2O$: 1.2 ml Toluene: 21.5 ml.

The contents of the autoclave were flushed with nitrogen and then many times with carbon monoxide. Thereafter, the contents were heated to 115° C. After the temperature is attained, the autoclave was pressurised to 800 psig with carbon monoxide, stirring started and it was observed that gas absorption commenced immediately. For synthesis of ibuprofen, the pressure in the autoclave was maintained constant using carbon monoxide and the progress of the reaction was monitored by observing the pressure drop and by liquid sampling. The reaction was continued until the pressure drop was too low. The reactor was then cooled and the liquid phase analyzed by gas chromatography.

The GC analysis showed TOF of 130 $h^{-1}$ and 97% conversion of 1-(4'-isobutylphenyl)ethyl chloride with ibuprofen selectivity of 98%. The catalyst was filtered out and the solvent evaporated and the reaction mixture re-dissolved in toluene. The precipitated solid portion, which is a mixture of LiCl and lithium salt of p-toluene sulphonic acid was filtered out. The filtrate was treated with saturated solution of sodium bicarbonate two–three times and the aqueous phase separated to obtain the sodium salt of ibuprofen, which on hydrolysis with acid and extraction with dichloromethane, evaporation and vacuum distillation gives the pure product.

Advantage of the Invention:

1. Employment of a novel heterogeneous catalyst under mild reaction conditions.

Provides high reaction rates

Provides very high selectivity to 2-aryl propionic acids.

Provides simple and efficient catalyst separation and recycle.

What is claimed is:

1. A process for the preparation of 2-aryl propionic acid of the formula III:

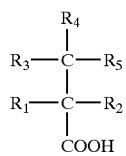

wherein $R_1$ is selected from the group consisting of phenyl, naphthyl, substituted phenyl and substituted napthyl; $R_2$, $R_3$, $R_4$ and $R_5$ are independently selected from the group consisting of hydrogen, methyl and substituted methyl; comprising the steps of:

carbonylating an aryl compound selected from an aryl alcohol, an aryl halide of formula I:

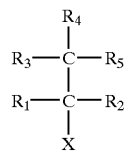

wherein $R_1$, $R_2$, $R_3$, $R_4$ and $R_5$ are as stated above; and X is selected from halogen and —OH group; or an aryl olefin of formula II:

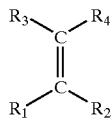

wherein $R_1$, $R_2$, $R_3$ and $R_4$ are as stated above; in the presence of a halide source, wherein the halide source comprises a halide salt selected from the group consisting of lithium chloride, sodium chloride, potassium chloride, lithium iodide, lithium bromide, sodium bromide, sodium iodide, potassium bromide; potassium iodide, tetrabutyl ammonium chloride, and tetrabutyl ammonium iodide and mixtures thereof, a protonic acid wherein the protonic acid comprises a hydrohalic acid selected from the group consisting of hydrochloric acid, hydrobromic acid, hydroiodic acid, para-toluene sulphonic acid, methane sulphonic acid, trifluoromethane sulphonic acid, formic acid, oxalic acid, acetic acid, trifluoroacetic acid and mixtures thereof, water and a catalyst system, wherein the catalyst system comprises a heterogeneous metal selected from the group consisting of palladium, platinum, rhodium, iridium, ruthenium, cobalt, nickel and mixtures thereof; a phoshpine ligand selected from the group consisting of triphenyl phosphine, tris(p-tolyl)phoshine, tricyclohexyl phosphine, tris(p-chloro phenyl)phosphine, tris(p-fluoro phenyl)phosphine, tris(p-methoxy phenyl)phosphine, tributyl phosphine, tris(isopropyl)phosphine, bisdiphenyl phosphino ethane, bisdiphenyl phosphino propane, bisdiphenyl phosphino butane and mixtures thereof; in an organic solvent wherein the organic solvent is selected from an aromatic hydrocarbon, wherein the aromatic hydrocarbon is selected from the group consisting of benzene, toluene, xylene and mixtures thereof; a ketone selected from methylethyl ketone and acetone, a cyclic ether selected from tetrahydrofuran and dioxan, nitrile and amide in carbon monoxide atmosphere, at a temperature in the range of 30 to 130° C., for a period in the range of 0.3 to 24 hours, at a pressure in the range of 50 to 1500 psig;

cooling the reaction mixture to an ambient temperature;
flushing the reaction vessel with an inert gas;
separating the catalyst system;
removing the solvent; and
isolating the δ-aryl propionic acid of formula III.

2. The process as claimed in claim 1, wherein the heterogeneous metal is in the form of metal powder or supported metal.

3. The process as claimed in claim 2, wherein the supported metal comprises a support selected from carbon or a refractory oxide, wherein the refractory oxide is selected from the group consisting of γ-alumina, silica, titania, zirconia, clays, zeolites and mixtures thereof.

4. The process as claimed in claim 1, wherein the nitrile is acetonitrile and the amide is N-methyl-pyrrolidone.

5. The process as claimed in claim 1, wherein the heterogeneous metal has a concentration of one mole for every 500 to 50,000 moles of the aryl compounds of formula I or II.

6. The process as claimed in claim 5, wherein the heterogeneous metal has a concentration of one mole for every 800 to 20,000 moles of the aryl compounds of formula I or II.

7. The process as claimed in claim 6, wherein the heterogeneous metal has a concentration of one mole for every 1,000 to 15,000 moles of the aryl compounds of formula I or II.

8. The process as claimed in claim 1, wherein the halide source is in an amount per gram mole of metal in the range of 50 to 10000 moles.

9. The process as claimed in claim 8, wherein the halide source is in an amount per gram mole of metal in the range of 100 to 8000 moles.

10. The process as claimed in claim 9, wherein the halide source is in an amount per gram mole of metal in the range of 500 to 6000 moles.

11. The process as claimed in claim 1, wherein the protonic acid is in an amount per gram mole of metal in the range of 50 to 10000 moles.

12. The process as claimed in claim 11, wherein the protonic acid is in an amount per gram mole of metal in the range of 100 to 8000 moles.

13. The process as claimed in claim 12, wherein the protonic acid is in an amount per gram mole of metal in the range of 500 to 6000 moles.

14. The process as claimed in claim 1, wherein the phosphine ligand is in an amount per gram mole of metal in the range of 20 to 250 moles.

15. The process as claimed in claim 1, wherein the water is in the range of 1 to 6% (v/v) of the total reaction mixture.

16. The process as claimed in claim 15, wherein the water is in the range of 3 to 5% (v/v) of the total reaction mixture.

17. The process as claimed in claim 1, wherein the reaction is carried out in a stirred reactor.

18. The process as claimed in claim 1, wherein the substituted phenyl is selected from the group consisting of 4-isobutylpbenyl, 4-methylphenyl, 4-chlorophenyl, 4-bromophenyl, 4-cyanomethyl, 4-tert butylphenyl, 4-hydroxyphenyl and mixtures thereof.

19. The process as claimed in claim 1, wherein the substituted naphthyl is 6-inethoxy naphthyl.

20. The process as claimed in claim 1, wherein the substituted methyl is methoxy methyl.

21. The process as claimed in claim 1, wherein X is chlorine.

* * * * *